United States Patent
Müller et al.

(10) Patent No.: US 6,232,475 B1
(45) Date of Patent: May 15, 2001

(54) PROCESS FOR PREPARING FLUORINE-CONTAINING PHENETHYLAMINES AND NOVEL FLUORINE-CONTAINING β-IMINOVINYL- AND β-IMINOETHYLBENZENES

(75) Inventors: Peter Müller, Bergisch Gladbach; Albrecht Marhold, Leverkusen, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/464,252

(22) Filed: Dec. 16, 1999

(30) Foreign Application Priority Data

Dec. 23, 1998 (DE) .............................................. 198 59 684

(51) Int. Cl.⁷ ..................... C07D 307/78; C07D 317/46; C07D 319/20; C07C 211/03
(52) U.S. Cl. .......................... 549/362; 549/366; 549/440; 549/467; 564/374
(58) Field of Search ..................................... 549/362, 366, 549/440, 467; 564/374

(56) References Cited

U.S. PATENT DOCUMENTS 5,936,089 * 8/1999 Carpino et al. .

OTHER PUBLICATIONS

Journal of American Chemical Society, vol. 63, Jan.–Jun. 1941, pp. 602–605, Suter et al. Some Fluorinated Amines of the Pressor Type.

Journal of Organic Chemistry, vol. 23, Jul.–Dec. 1958, pp. 1979–1984, Benington et al, Psychopharmacological Activity of Ring–and Chain–Substituted β–Phenethylamines.

Journal of Organic Chemistry, vol. 58, Jun. 4, 1993, pp. 3299–3303, Busacca et al., Phenethylamines via Heck Arylation of a New Vinylamine Equivalent.

Journal of Organic Chemistry, Bd. 43, Nr. 15, 1978 Seiten 2949–2952, XP002134569, C. B. Ziegler, Jr. et al., "Palladium–Catalyzed Vinylic Substitution Reactions of N–Vinyl Amides."

Journal of Organic Chemistry, Bd. 57, Nr. 13, 1992 Seiten 3558–3563, XP002134568, Walter Cabri et al. "Palladium–catalyzed Arylation of Unsymmetrial Olefins. Bidentate Phosphine Ligand Controlled Regioselectivity".

* cited by examiner

*Primary Examiner*—Joseph K. McKane
*Assistant Examiner*—Taofiq A. Solola
(74) *Attorney, Agent, or Firm*—Joseph C. Gil; Diderico van Eyl

(57) ABSTRACT

The present invention relates to a process for preparing fluorine-containing phenethylamines which is characterized in that, in a first step, a substituted bromobenzene is reacted with an N-vinylimide in the presence of a palladium catalyst, in a second step, the resulting substituted β-iminovinylbenzene is hydrogenated catalytically and in a third step, the substituted β-iminovinylbenzene obtained in the second step is cleaved. This process also provides access to novel β-iminovinyl- and β-iminoethylbenzenes.

8 Claims, No Drawings

PROCESS FOR PREPARING FLUORINE-CONTAINING PHENETHYLAMINES AND NOVEL FLUORINE-CONTAINING β-IMINOVINYL- AND β-IMINOETHYLBENZENES

SUMMARY OF THE INVENTION

The present invention relates to a novel process for preparing fluorine-containing phenethylamines and to novel chemical compounds resulting from this process.

BACKGROUND OF THE INVENTION

4-Fluorophenethylamine and other fluorine-containing substituted phenethylamines are interesting intermediates, for example for preparing agrochemicals. J. Am. Chem. Soc. 63, 602 (1941) discloses that 4-fluorophenethylamines can be prepared in a multi-step process. Here, p-fluorophenethyl alcohol is obtained starting from p-fluorophenylmagnesium bromide by addition to ethylene oxide with subsequent hydrolysis and converted with phosphorus tribromide into p-fluorophenylethyl bromide which is hydrolyzed with ammonia to give the target product. Disadvantages of using this process, especially on a relatively large scale, are, in addition to the large number of steps involved, the technical expense required for carrying out a Grignard reaction, including the required safety measures, and the use of phosphorus tribromide which is costly and the handling of which likewise requires high expenditure for safety measures. Alternatively, according to J. Org. Chem. 23, 1979 (1958), it is also possible to use p-fluorobenzyl chloride as starting material, which is reacted with sodium cyanide to give p-fluorophenylacetonitrile which is then reduced using sodium alanate. If this route was to be realized on an industrial scale, the use of the highly toxic sodium cyanide would require particular safety measures. The use of sodium alanate, which is known to react explosively with halogenated hydrocarbons (see Römpp Lexikon Chemie Version 1.3 on CD-ROM (1997)), renders this process completely useless for industrial application.

N-[2-(Fluorophenyl)-ethenyl]-phthalimide is disclosed in J. Org. Chem. 58, 3299 (1993). In this publication, it is described as being obtainable from an iodine compound. This process is uneconomical. It was contrary to expectations that this and other fluorine-containing β-iminovinylbenzenes could be obtainable in a simple manner.

DETAILED DESCRIPTION OF THE INVENTION

This invention, accordingly, provides a process for preparing fluorine-containing phenethylamines of the formula (I)

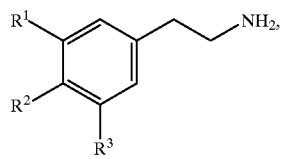

in which one of the radicals
R$^1$ and R$^2$ represents fluorine, trifluoromethyl, trifluoromethoxy, tetrafluoroethoxy or pentafluoroethoxy and the other represents hydrogen, C$_1$–C$_6$-alkyl, C$_1$–C$_6$-alkoxy, fluorine, trifluoromethyl, trifluoromethoxy, tetrafluoroethoxy or pentafluoroethoxy or
R$_1$ and R$^2$ together represent —O—CF$_2$—O—, —O—CF$_2$—CF$_2$— or —O—CF$_2$—CF$_2$—O— and
R$^3$ represents hydrogen, C$_1$–C$_6$-alkyl or C$_1$–C$_6$-alkoxy,
characterized in that in a first step a substituted bromobenzene of the formula

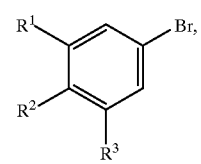

(IV)

in which
R$_1$, R$^2$ and R$^3$ are each as defined under formula (I), is reacted with an N-vinylimide of the formula

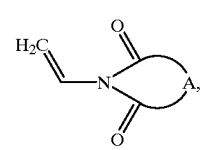

(V)

in which
A represents —CH$_2$—CH$_2$—, —CH$_2$—CH$_2$—CH$_2$—, —CH$_2$—C(CH$_3$)$_2$—CH$_2$—, —CH$_2$—O—CH$_2$—, —CH=CH— or o-phenylene,
in the presence of a palladium catalyst, the resulting β-iminovinylbenzene of the formula

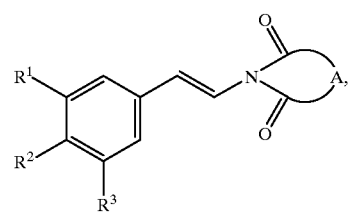

(III)

in which
the radicals R$^1$, R$^2$ and R$^3$ are each as defined under formula (I) and the radical A is as defined under formula (V),
is, in a second step, hydrogenated catalytically and, in a third step, the substituted β-iminoethylbenzene of the formula

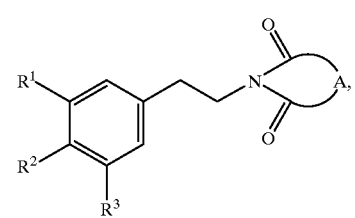

(II)

in which
R$^1$, R$^2$ and R$^3$ are each as defined under formula (I) and the radical A is as defined under formula (V), which is obtained in the second step, is cleaved.

In the formulae (I), (II), (III) and (IV), one of the radicals
$R^1$ and $R^2$ preferably represents a radical from the group consisting of fluorine, trifluoromethyl, trifluoromethoxy, tetrafluorethoxy or pentafluoroethoxy and the other radical preferably represents hydrogen or $R^1$ and $R^2$ preferably together represent —O—$CF_2$—O—, —O—$CF_2$—$CF_2$— or —O—$CF_2$—$CF_2$—O—.

$R^3$ preferably represents hydrogen.

A in the formulae (II), (III) and (V) preferably represents —$CH_2$—$CH_2$— or o-phenylene.

Particularly preferably, in the formulae (I), (II), (III) and (IV)

$R^1$ and $R^3$ represent hydrogen and $R^2$ represents fluorine, trifluoromethyl or trifluoromethoxy or $R^1$ represents fluorine, trifluoromethyl or trifluoromethoxy and $R^2$ and $R^3$ represent hydrogen or R1 and R2 together represent —O—CF2—O—, —O—CF2—CF2— or —O—CF2—CF2—O— and R3 represents hydrogen.

In the formulae (II), (III) and (V), A particularly preferably represents o-phenylene.

The tetrafluoroethoxy radicals are preferably 1,1,2,2-tetrafluoroethoxy radicals.

Very particular preference according to the invention is given to the fluorine-containing phenethylamines listed in Table 1.

Suitable palladium catalysts for the first reaction step are, for example, palladium complexes having aryl- or alkylphosphine ligands. It is possible to use both the complexes, and palladium(II) salts and the free ligands. Preference is given to using palladium(II) acetate and tri-o-tolylphosphine.

Suitable diluents for the first reaction step are dipolar solvents and mixtures comprising these, for example with aliphatic and/or aromatic hydrocarbons and/or ethers. Examples of dipolar solvents are: nitriles, such as acetonitrile, propionitrile, n- and i-butyronitrile and benzonitrile, amides, such as formamide, N-methylformamide, N,N-dimethylformamide, N,N-dimethylacetamide and N-methyl-pyrrolidone, esters, such as methyl, ethyl and butyl acetate, sulphoxides, such as dimethyl sulphoxide, and sulphones, such as sulpholane. It is also possible to use mixtures of dipolar solvents.

Suitable reaction auxiliaries for the first reaction step are, for example, weak inorganic or organic bases. Preference is given to alkaline earth metal and alkali metal acetates, carbonates and bicarbonates, such as sodium acetate, potassium acetate, calcium acetate and ammonium acetate, sodium carbonate, potassium carbonate and ammonium carbonate, sodium bicarbonate and potassium bicarbonate, and tertiary amines, such as trimethylamine, triethylamine and tributylamine. Preference is given to using sodium acetate or potassium acetate.

For carrying out the first reaction step, the respective bromobenzene of the formula (IV) and the respective N-vinylimide of the formula (V) can be employed, for

TABLE 1

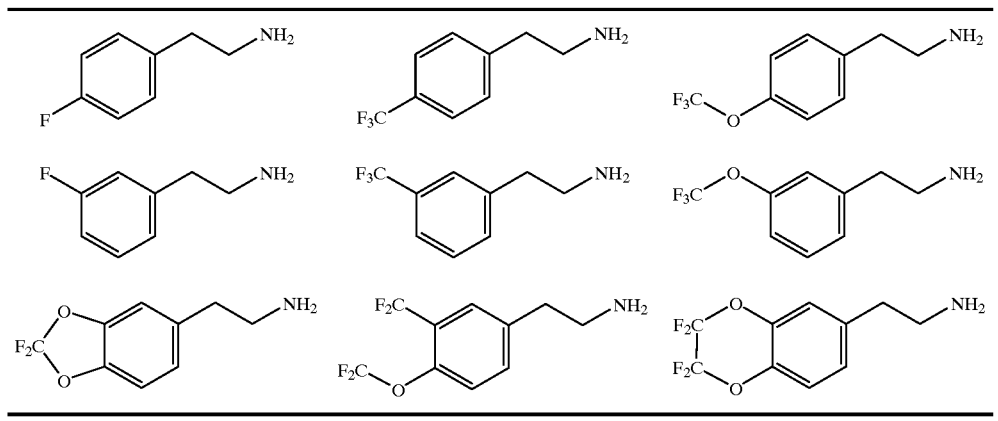

The reaction of the bromobenzenes of the formula (IV) with N-vinylimides of the formula (V) to give the β-iminovinylbenzenes of the formula (III) is carried out in the presence of a palladium catalyst, preferably in the presence of diluents and reaction auxiliaries.

From among the N-vinylimides of the formula (V), N-vinylphthalimide and N-vinyl-succinimide, for example, are commercially available. N-Vinylmaleimide, for example, is obtainable according to Macromol. Rapid Commun. 15, 867–872 (1994). N-Vinylglutarimide and N-vinyldiglycolimide are likewise known and obtainable in a known manner. N-Vinyl-3,3-dimethylglutarimide can be prepared analogously to the succinimide or the glutarimide, from the corresponding, commercially available dicarboxylic acid.

The bromobenzenes of the formula (IV) are either commercially available or known from the literature and obtainable according to general processes of the chemistry of aromatic compounds.

example, in amounts of from 0.5 to 2 mol of bromobenzene, based on 1 mole of N-vinylimide. This amount is preferably from 0.9 to 1.1 mol. Particular preference is given to using equimolar amounts of bromobenzene of the formula (IV) and N-vinylimide of the formula (V). Based on the bromobenzene, it is possible to use, for example, from 0.01 to 20 mmol, preferably from 0.1 to 10 mmol, of palladium catalyst and from 1 to 10 equivalents, preferably from 1 to 3 equivalents, of reaction auxiliary. If a palladium(II) salt and free phosphine ligands are employed separately, the molar ratio of palladium(II) salt to phosphine ligands can be, for example, from 1:1.5 to 1:10, preferably from 1:2 to 1:4. The amount of diluent is not critical. Preference is given to using from 100 to 2000 ml per mole of bromobenzene of the formula (IV).

The reaction temperature in the first process step can be varied within a relatively wide range. It can be, for example, between 50 and 180° C., preferably between 80 and 150° C.

The catalytic hydrogenation of β-phthaliminovinylbenzenes of the formula (III) to give β-phthaliminoethylbenzenes of the formula (II) is carried out, inter alia, using hydrogen gas, preferably in the presence of a diluent.

Suitable catalysts for carrying out this hydrogenation are, for example, supported noble metals, in particular palladium and platinum on carbon, silicates, silica, alumina, zeolites, barium sulphate, calcium carbonate and spinels. Particular preference is given to palladium on carbon. Based on the finished catalyst, it may comprise, for example, from 0.1 to 20% by weight of noble metal. This amount is preferably from 5 to 15% by weight.

Suitable diluents for the secornd reaction step are water, organic solvents and any mixtures of these. Examples of organic solvents which may be mentioned are: aliphatic, alicyclic and aromatic hydrocarbons, such as petroleum ether, hexane, heptane, cyclohexane, methylcyclohexane, benzene, toluene, xylene and decalin, ethers, such as diethyl ether, diisopropyl ether, methyl t-butyl ether and methyl t-amyl ether, dioxane, tetrahydrofuran, 1,2-dimethoxyethane, 1,2-diethoxyethane, diethyl glycol dimethyl ether and anisole, esters, such as methyl acetate, ethyl acetate or butyl acetate, and alcohols, such as methanol, ethanol, n- and i-propanol, n-, iso-,sec- and tert-butanol, ethanediol, propane-1,2-diol, ethoxyethanol, methoxyethanol, diethylene glycol monomethyl ether and diethylene glycol monoethyl ether. The preferred solvent is tetrahydrofuran.

For carrying out the second reaction step, it is possible to use, for example, from 0.01 to 0.5 mol, preferably from 0.05 to 0.2 mol, of catalyst (calculated as metal) and from 1 to 10 l of diluent per mole of β-iminovinylbenzene of the formula (III). It is possible to use the catalyst repeatedly in successive reactions. In batches with catalyst which has already been used, the reaction time may be prolonged. This can be compensated by addition of fresh catalyst, for example in an amount of from 5 to 25% by weight, based on the total amount of catalyst used.

The reaction temperature for the second reaction step can be varied within a relatively wide range. It can be, for example, between 0 and 100° C., preferably between 20 and 70° C. The hydrogen pressure can be, for example, between 1 and 100 bar, preferably between 5 and 50 bar.

The cleavage of the B-phthaliminoethylbenzenes of the formula (II) to give the phenethylamines of the formula (I) can be carried out, for example, using an aqueous base. Suitable bases are, for example, hydrazine hydrate and aqueous alkali metal hydroxides. Preference is given to using hydrazine hydrate, if appropriate in combination with an aqueous alkali metal hydroxide. If hydrazine hydrate and an aqueous alkali metal hydroxide are used, it is preferred to initiate the cleavage with hydrazine hydrate and to add the aqueous alkali metal hydroxide later.

It is possible to use, for example, from 1.2 to 5 equivalents of hydrazine and, if appropriate, from 1 to 30 mol of aqueous alkali metal hydroxide per mole of β-phthaliminoethylbenzene of the formula (II). Preference is given to adding initially from 1.5 to 3 equivalents of hydlrazine hydrate and later from 5 to 20 mol of aqueous alkali metal hydroxide per mole of β-phthaliminoethylbenzene of the formula (II). Among the alkali metal hydroxides, potassium hydroxide is preferred.

The temperature in the imide cleavage can be varied within a wide range. In general, the reaction is carried out at elevated temperature. The upper limit of the temperature is the boiling point of the reaction mixture. Preference is given to carrying out the reaction at from 50 to 100° C.

The proportion of water in the base which is employed can be. for example, between 30 and 70% by weight, preferably between 40 and 60% by weight.

The reactions of the first and the third step of the process according to the invention can be carried out under atmospheric pressure or under elevated pressure. Preference is given to operating under atmospheric pressure.

The practice of the reaction, ind the work-up and the isolation of the reaction products can be carried out by generally customary known methods. The end products are preferably purified by crystallization, distillation or by removing the volatile components, if appropriate under reduced pressure.

The present invention furthermore relates to β-iminovinylbenzenes of the formula

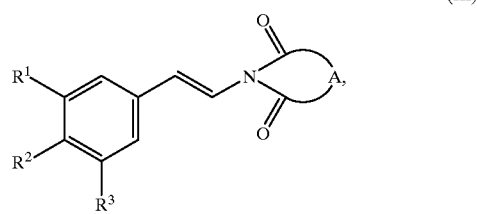

(III)

in which
R$^1$, R$^2$, R$^3$ and A each have the broadest meaning given above, except for the compound N-[2-(3-fluorophenyl)-ethenyl]-phthalimide. The preferred and particularly preferred meanings of these radicals also correspond to those given above.

Finally, the present invention also relates to β-iminoethylbenzenes of the formula

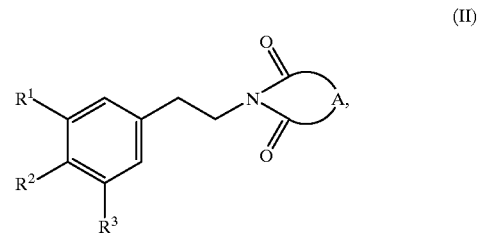

(II)

in which
R$^1$, R$^2$, R$^3$ and A each have the broadest meaning given above. The preferred and particularly preferred meanings of these radicals also correspond to those given above.

The novel β-iminovinyl- and β-iminoethylbenzenes can be prepared as described above and be employed as intermediates, which do not always have to be isolated, for preparing fluorine-containing phenethylamines of the formula (I). In particular at the stage of the β-iminoethylbenzenes of the formula (II), isolation of the intermediate may be dispensed with.

Using the process according to the invention, it is possible to prepare fluorine-containing phenethylamines in a three-step process where the individual steps can be realized with yields of 80% or more. The process according to the invention also provides, for the first time, a process for preparing fluorine-containing phenethyl-amines which can also be realized in a simple manner on an industrial scale. Particular safety measures are not required.

The discovery of the β-iminovinyl- and β-iminoethylbenzenes according to the invention was the essential precondition for the process according to the invention to be conceived in the scope outlined here.

J. Org. Chem. 58, 3299 (1993) does not suggest the existence of other fluorine-containing β-iminovinylbenzenes, since it only describes a process for preparing an individual β-iminovinylbenzene, which process is neither industrially nor economically of interest.

EXAMPLES

Example 1

N-[2-(4-Trifluorornethoxyphenyl)ethenyl]phthalimide 275 ml of dry dimethylformamide were flushed with nitrogen for 1 hour. 100 g of 1-bromo-4-trifluoromethoxybenzene, 71.8 g of N-vinylphthalimide, 94.4 mg of palladium(II) acetate, 508 mg of tri(o-tolyl)phosphine and 67.8 g of sodium acetate were added successively, and the mixture was stirred at 130° C. for 24 hours. After cooling, the mixture was filtered and the filtrate was concentrated. The filtration residue was combined with the concentrated filtrate, and the mixture was suspended in 300 ml of water and filtered again. The filtration residue which was then present was washed with a further 500 ml of water and pressed dry. The crude product was suspended in 200 ml of n-hexzte and heated at the boil for 1 hour. The hot mixture was filtered and the filter cake was dried. This gave 126.9 g of product. According to GC, stated in area percent, the product was 92% pure. This corresponds to a yield of 84% of theory.

Example 2

N-[2-(4-Trifluoromethoxyphenyl)-ethyl]phthalimide

In a stirred autoclave, 200 g of the product obtained according to Example 1 were initially charged dissolved in 500 ml of tetrahydrofuran, 16 g of palladium on carbon (10% by weight) were added and the mixture was hydrogenated at 50° C. and a hydrogen pressure of 10 bar until complete conversion had occurred (about 30 hours). The catalyst was then filtered off and the solvent was removed. This gave 190 g of product. According to GC, stated in area percent, the product was 90% pure. The yield was 85% of theory.

This examples was repeated twice, using in each case 85% by weight of catalyst which had already been used and 15% by weight of fresh catalyst. The yield of product remained virtually constant.

Example 3

2-(4-Trifluoromelhoxyphenyl)ethylamine 475 g of the product obtained according to Example 2 were initially charged in 2500 ml of toluene, the mixture was heated to 75° C. 89 g of hydrazine monohydrate were then added dropwise. The mixture was stirred under reflux for 8 hours. At 75° C., 1000 g of 50% by weight strength aqueous potassium hydroxide solution were then added dropwise to the suspension, and stirring under reflux was continued for a further 4 hours. After cooling, the aqueous (heaviest) phase and an organic oily (middle) phase were separated off. The toluene, as lightest organic phase, was slowly distilled off and the residue was distilled under reduced pressure using a short Vigreux column. 216 g of product were obtained, which distilled over at from 84 to 86° C./11 mbar. According to GC, stated in area per cent, the product was 99% pure. This corresponds to a yield of 80% of theory.

Example 4

Preparation of the Intermediate N-vinylphthalimide (not according to the invention)

Over a period of 2 hours, 672 g of 1,8-diazabicyclo-[5.4.0]-undec-7-ene were added dropwise to a solution of 1016 g of N-(2-bromoethyl)phthalimide in 2.8l of N,N-dimethylacetamide. During the addition, the temperature increased to 60° C. After the addition had ended, stirring was continued for 12 hours. The batch was poured into 9 l of water and filtered, and the filtration residue was dried at 50° C. This gave 621 g of product (=90% of theory) of melting point 79–80° C.

Example 5

N-{2-[3,4-Bis(trifluoromethoxy)phenyl]ethenyl}phthalimide 7.3 l of dry dimethylformamide were flushed with nitrogen for 1 hour. 2.71 kg of 1-bromo-3,4-bis(trifluoromethoxy)benzene, 1.95 kg of N-vinylphthalimide, 2.52 g of palladium(II) acetate, 13.7 g of tri-(o-tolyl)phosphine and 1.84 kg of sodium acetate were added successively, and the mixture was stirred at 130° C. for 30 hours. After cooling, the mixture was filtered and the filtrate was concentrated. The filtration residue was combined with the concentrated filtrate, and the mixture was suspended in 27 l of water and filtered again. The filtration residue which was then present was washed with 5 l of n-hexane and pressed dry. This gave 2.9 kg of product of melting point 159–160° C. According to GC, stated in area per cent, the product was 90.5% pure. This corresponds to a yield of 70% of theory.

Example 6

N-{2-[3,4-Bis(trifluoromethoxy)phenyl]ethyl}phthalimide

In a stirred autoclave, 5.65 kg of the product obtained from two batches according to Example 21 were initially charged dissolved in 14 kg of tetrahydrofuran, 452 g of palladium on carbon (10% by weight) were added and the mixture was hydrogenated at 50° C. and a hydrogen pressure of from 5 to 10 bar until the reaction had gone to completion (about 8 hours). The catalyst was then filtered off and the solvent was removed. This gave 5 kg of product of melting point 91–93° C. According to GC, stated in area per cent, the product was 97.8% pure. The yield was 97% of theory.

This example was repeated twice, using in each case 85% by weight of catalyst which had already been used and 15% by weight of fresh catalyst. The yield of product remained virtually constant.

Example 7

2-[3,4-Bis(trifluoromethoxy)phenyl]ethylamine 500 g of the product obtained according to Example 6 were initially charged in 950 ml of toluene, and the mixture was heated to 75° C. 171.3 g of hydrazine monohydrate were then added dropwise. The mixture was stirred at from 70 to 80° C. for 8 hours. 470 g of 30% by weight strength aqueous potassium hydroxide solution were then added dropwise, and stirring was continued for a further 60 min. After cooling the aqueous (heaviest) phase and an organic oily (middle) phase were separated off. The toluene, being the lightest organic phase, was slowly distilled off, and the residue was distilled under reduced pressure using a short Vigreux column. 231.1 g of product, which distilled over at from 85 to 86° C./11 mbar, were obtained. According to GC, stated in area per cent, the product was 99.6% pure. This corresponds to a yield of 89% of theory.

Example 8

Preparation of the Intermediate N-vinylphthalimide (not according to the invention)

Over a period of 2 hours, 2.3 g of 1,8-diazabicyclo-[5.4.0]-undec-7-ene were added dropwise to a solution of 3.5 kg of N-(2-bromoethyl)phthalimide in 9.6 l of N,N-dimethylacetamide. During the addition, the temperature increased to 50° C. After the addition had ended, stirring was continued for 17 hours. The batch was poured into 29 l of water and filtered, and the filtration residue was dried at from 30 to 40° C. This gave 1.95 kg of product (=82% of theory) of melting point 79–80° C.

Example 9

N-[2-(3-Trifluoromethylphenyl)ethylenyl]phthalimide 148 ml of dry dimethylformaruide were flushed with nitrogen for 1 hour. 50 g of 1-bromo-3-trifluoromethylbenene, 38.4 g of N-vinylphthalimide, 503 mg of palladium(II) acetate and 2.72 g of tri(o-tolyl) phosphine were added successively. At 110° C., 29.1 g of triethylamine were added dropwise over a period of 7 h. After the addition had ended, the mixture was stirred at 110° C. for 20 hours. After cooling, the reaction mixture was concentrated and the residue was stirred with 300 ml of water and 100 ml of methanol. The mixture was filtered and the filtration residue was washed with 500 ml of water and pressed dry. This gave 55.3 g of product of melting point 139–141° C. According to GC, stated in area per cent, the product was 75.5% pure. This corresponds to a yield of 59% of theory.

Example 10

N-[2-(3-Trifluoromethylphenyl)ethyl]phthalimide

In a stirred autoclave, 50 g of the product obtained according to Example 9 were initially charged dissolved in 150 ml of tetrahydrofiran, 2 g of palladium on carbon (10% by weight) were added and the mixture was hydrogenated at 100° C. and a hydrogen pressure of 50 bar until the reaction had gone to completion (about 21 hours). The catalyst was then filtered off and the solvent was removed. This gave 44 g of product of melting point 69–71° C. According to GC, stated in area per cent, the product was 76.6% pure. The yield was 84% of theory.

Example 11

2-(3-Trifluoromethylphenyl)ethylamine 39.5 g of the product obtained according to Example 10 were initially charged in 80 ml of toluene, and the mixture was heated to 75° C. 16.2 g of hydrazine monohydrate were then added dropwise. The mixture was stirred at 75° C. for 3 hours.

37.8 g of 25% by weight strength aqueous potassium hydroxide solution were then added dropwise, and the mixture was stirred for a further 30 min. After cooling, the aqueous (heaviest) phase and an organic oily (middle) phase were separated off. The toluene, being the lightest organic phase, was slowly distilled off and the residue was distilled under reduced pressure using a short Vigreux column. 10.5 g of product, which distilled over at from 78 to 80° C./15 mbar, were obtained. According to GC, stated in area per cent the product was 97.3% pure. This corresponds to a yield of 60% of theory.

Example 12

N-[2-(4-Trifluorcmethylphenyl)ethenyl]phthalimide 138 ml of dry dimethylformamide were flushed with nitrogen for 20 minutes. 50 g of 1-bromo-4-trifluoromethylbenzene, 38.4 g of N-vinylphthalimide, 54.2 mg of palladium(II) acetate, 67.6 mg of tri(o-tolyl) phosphine and 36.4 g of sodium acetate were added successively, and the mixture was stirred at 130° C. for 12 hours. After cooling, the mixture was filtered and the filtrate was concentrated. The filtration residue was combined with the concentrated filtrate, and the mixture was suspended in 150 ml of water and filtered again. The filtration residue which was then present was washed successively with 250 ml of water and 100 ml of n-hexane and pressed dry. This gave 36.5 g of product of melting point 201–205° C. According to GC, stated in area per cent, the product was 86.2% pure. This corresponds to a yield of 44% of theory.

Example 13

N-[2-(4-Trifluoromethylphenyl)ethyl]phthalimide

In a stirred autoclave, 31 g of the product obtained according to Example 12 were initially charged dissolved in 300 ml of tetrahydrofuran, 2 g of palladium on carbon (10% by weight) were added and the mixture was hydrogenated at 80° C. and a hydrogen pressure of 60 bar until the reaction had gone to completion (about 8 hours). The catalyst was then filtered off and the solvent was removed. This gave 32.8 g of product of melting point 134–135° C. According to GC, stated in area per cent, the product was 83.2% pure. The yield was 87% of theory.

Example 14

2-(4-Trifluorometlhylphenyl)ethylamine 31.3 g of the product obtained according to Example 13 were initially charged in 80 ml of toluene, and the mixture was heated to 75° C. 13.1 g of hydrazine monohydrate were then added dropwise. The mixture was stirred at 75° C. for 3 hours. 30.7 g of 25% by weight strength aqueous potassium hydroxide solution were then added dropwise and stirring was continued for a further 30 min. After cooling, the aqueous (heaviest) phase and an organic oily (middle) phases were separated off. The toluene, being the lightest organic phase, was slowly distilled off and the residue was distilled under reduced pressure using a short Vigreux column. 9 g of product, which distilled over at from 81 to 82° C./12 mbar, were obtained. According to GC, stated in area per cent, the product was 97.6% pure. This corresponds to a yield of 57% of theory.

Example 15

N-[2-(4-Fluorophenyl)ethenyl]phthalimide 190 ml of dry dimethylformamide were flushed with nitrogen for 20 minutes. 44.3 g of 1-bromo-4-fluorobenzene, 43.9 g of N-vinylphthalimide, 568 mg of palladium(II) acetate and 3.1 g of tri(o-tolyl)phosphine were added successively. At 130° C., 33.2 g of triethylamine were added dropwise. After the addition had ended, the mixture was stirred at 130° C. for 12 hours. After cooling, the reaction mixture was concentrated and the residue was suspended in 200 ml of water and filtered. The filtration residue which was then present was washed successively with 200 ml of water and 100 ml of n-hexane and pressed dry. This gave 41 g of product of melting point 151–152° C. According to GC, stated in area per cent, the product was 96.4% pure. This corresponds to a yield of 58% of theory.

Example 16

N-[2-(4-Fluorophenyl)ethyl]phthalimide

In a stirred autoclave, 37 g of the product obtained according to Example 15 were initially charged dissolved in 380 ml of tetrahydrofuran, 1.5 g of palladium on carbon (10% by weight) were added and the mixture was hydrogenated at 60° C. and a hydrogen pressure of 50 bar until the reaction had gone to completion (about 21 hours). The catalyst was then filtered off and the solvent was removed. This gave 36.1 g of the product of melting point 106–107° C. According to GC, stated in area per cent, the product was 92.1% pure. The yield was 95% of theory.

Example 17

2-(4-Fluorophenyl)ethylamine 34.6 g of the product obtained according to Example 16 were initially charged in 80 ml of toluene and the mixture was heated to 75° C. 17.6 g of hydrazine monohydrate were then added dropwise. The mixture was stirred at 75° C. for 3 hours. 41.6 g of 25% by weight strength aqueous potassium hydroxide solution were then added dropwise and stirring was continued for a further 30 min. After cooling, the aqueous (heaviest) phase and an organic oily (middle) phase were separated off. The toluene, being the lightest organic phase, was slowly distilled off and the residue was distilled under reduced pressure using a short Vigreux column. 12 g of product, which distilled over at from 83 to 85° C./16 mbar, were obtained. According to GC, stated in area per cent, the product was 96.3% pure. This corresponds to a yield of 70% of theory.

Example 18

N-[2-(3-Fluorophenyl)ethenyl]phthalimide 190 ml of dry dimethylformamide were flushed with nitrogen for 20 minutes. 44.3 g of 1-bromo-3-fluorobenzene, 43.9 g of N-vinylphthalimide, 568 mg of palladium(II) acetate and 3.1 g of tri(o-tolyl)phosphine were then added successively. At 130° C., 33.2 g of triethylamine were added dropwise. After the addition had ended, the mixture was stirred at 130° C. for 16 hours. After cooling, the reaction mixture was concentrated and the residue was suspended in 200 ml of water and filtered. The filtration residue which was then present was washed successively with 200 ml of water and 100 ml of n-hexane and pressed dry. This gave 47.2 g of product of melting point 175 to 177° C. According to GC, stated in area per cent, the product was 86.7% pure. This corresponds to a yield of 60% of theory.

Example 19

N-[2-(3-Fluorophenyl)ethyl]phthalimide

In a stirred autoclave, 43.2 g or the product obtained according to Example 18 were initially charged dissolved in 300 ml of tetrahydrofuran, 1 g of palladium on carbon (10% by weight) was added and the mixture was hydrogenated at 100° C. and a hydrogen pressure of 50 bar until the reaction had gone to completion (about 37 hours). The catalyst was then filtered off and the solvent was removed. This gave 41 g of product of melting point 122–125° C. According to GC, stated in area per cent, the product was 86% pure. The yield was 81% of theory.

Example 20

2-(3-Fluorophenyl)ethylamine 37.4 g of the product obtained according to Example 19 were initially charged in 80 ml of toluene and the mixture was heated to 75° C. 18.9 g of hydrazine monohydrate were then added dropwise. The mixture was stirred at 75° C. for 3 hours. 44.9 g of 25% by weight strength aqueous potassium hydroxide solution were then added dropwise and stirring was continued for a further 30 min. After cooling, the aqueous (heaviest) phase and an organic oily (middle) phase were separated off. The toluene, being the lightest organic phase, was slowly distilled off and the residue was distilled under reduced pressure using a short Vigreux column. This gave 10.6 g of product which distilled over at fiom 79 to 81° C./15 mbar. According to GC, stated in area per cent, the product was 94.7% pure. This corresponds to a yield of 52% of theory.

Example 21

N-{2-[(3,4-Bis(trifluoromethoxy)phenyl]ethenyl}phthalimide 160 ml of dry dimethylformamide were flushed with nitrogen for 20 minutes. 90 g of 1-bromo-3,4-bis(trifluoromethoxy)benzene, 48 g of N-vinylphthalimide, 33.8 mg of palladium(II) acetate, 84.2 mg of tri(o-tolyl)phosphine and 45 g of sodium acetate were then added successively and the mixture was stirred at 130° C. for 24 hours. After cooling, the mixture was filtered and the filtrate was concentrated. The filtration residue was combined with the concentrated filtrate, and the mixture was suspended in 1 l of water and -Filtered again. The filtration residue which was then present was washed with 200 ml of n-hexane and pressed dry. This gave 92 g of product of melting point 162–164° C. According to GC, stated in area per cent, the product was 93.5% pure. This corresponds to a yield of 74% of theory.

Example 22

N-{2-[3,4-Bis(trifluoromethoxy)phenyl]ethyl}phthalimide

In a stirred autoclave, 90 g of ithe product obtained according to Example 21 were initially charged dissolved in 280 ml of tetrahydrofuran, 2 g of palladium on carbon (10% by weight) were added and the mixture was hydrogenated at 50° C. and a hydrogen pressure of 10 bar until the reaction had gone to completion (about 24 hours). The catalyst was then filtered off and the solvent was removed. This gave 84 g of product of melting point 60–61 °C. According to GC, stated in area per cent, the product was 90% pure. The yield was 84% of theory.

Example 23

2-[3,4-Bis(trifluoromethoxy)phenyl]ethylamine 66.7 g of the product obtained according to Example 22 were initially charged in 125 ml of toluene and the mixture was heated to 75° C. 21.5 g of hydrazine monohydrate were then added dropwise. The mixture was stirred at 75° C. for 8 hours. 53.9 g of 25% by weight strength aqueous potassium hydroxide solution were then added dropwise and stirring was continued for a further 30 min. After cooling, the aqueous (heaviest) phase and an organic oily (middle) phase were separated off. The toluene, being the lightest organic phase, was slowly distilled off and the residue was distilled under reduced pressure using a short Vigreux column. This gave 35.8 g of product which distilled over at from 97 to 98° C./20 mbar. According to GC, stated in area per cent, the product was 99.3% pure. This corresponds to a yield of 85% of theory.

Example 24

N-[2-(2,2-Difluorobenzene[1,3]dioxol-5-yl)ethenyl]phthalimide 150 ml of dry dimethylformamide w,ere flushed with nitrogen for 20 minutes. 32.6 g of 5-bromo-2,2-difluorobenzo-1,3-clioxole, 24.6 g of N-vinylphthalimide, 315 mg of palladium(II) acetate, 1.72 mg of tri(o-tolyl) phosphine and 23 g of sodium acetate were added successively, and the mixture was stirred at 130° C. for 24 hours. After cooling, the mixture was filtered and the filtrate was concentrated. The filtration residue was combined with the concentrated filtrate, and the mixture was suspended in 500 ml of water and filtered again. The filtration residue which was then present was washed with 100 ml of n-hexane and pressed dry. This gave 25.8 g of product of melting point 162–164° C. According to GC, stated in area per cent, the product was 94% pure. This corresponds to a yield of 54% of theory.

Example 25

N-[2-(2,2-Difluorobenzene[1,3]dioxol-5-yl)ethyl]phthalimide

In a stirred autoclave, 24.2 g of the product obtained according to Example 24 were initially charged dissolved in 60 ml of tetrahydrofuran, 2 g of palladium on carbon (10% by weight) were added and the mixture was hydrogenated at 50° C. and a hydrogen pressure of 10 bar until the reaction had gone to completion (about 6 hours). The catalyst was then filtered off and the solvent was removed. This gave 22.5 g of product. According to GC, stated in area per cent, the product was 44% pure. The yield was 41% of theory.

Example 26

2-(2,2-Difluorobenzenie [1,3]dioxol-5-yl)ethylamine 21 g of the product obtained according to Example 25 were initially charged in 80 ml of toluene and the mixture was heated to 75° C. 8.5 g of hydrazine monohydrate were then added dropwise. The mixture was stirred at 75° C. for 3 hours. 20 g of 25% by weight strength aqueous potassium hydroxide solution were then added dropwise and stirring was continued for a further 30 min. After cooling, the aqueous (heaviest) phase and an organic oily (middle) phase were separated off. The toluene, being the lightest organic phase, was slowly distilled off. The residue was suspended in 50 ml of n-hexane and filtered. The filtrate was subsequently concentrated. This gave 3.7 g of product. According to GC, stated in area per cent, the product was 87% pure. This corresponds to a yield of 58% of theory.

Example 27

N-[2-(2,2,3,3-Tetrafluorobenzene[1,4]dioxin-6-yl)ethenyl]phthalimide 150 ml of dry dimethylformamide were flushed with nitrogen for 20 minutes. 39.5 g of 6-bromo-2,2,3,3-tetrafluorobenzo-1,4-dioxine, 24.6 g of N-vinylphthalimide, 315 mg of palladium(II) acetate, 1.72 mg of tri(o-tolyl) phosphine and 23 g of sodium acetate were added successively, and the mixture was stirred at 130° C. for 20 hours. After cooling, the mixture was filtered and the filtrate was concentrated. The filtration residue was combined with the concentrated filtrate, and the mixture was suspended in 500 ml of water and filtered again. The filtration residue which was then present was washed with 100 ml of n-hexane and pressed dry. This gave 44.3 g of product. According to GC, stated in area per cent, the product was 98.5% pure. This corresponds to a yield of 83% of theory.

Example 28

N-[2-(2,2,3,3-Tetrafluorobenzene[1,4]dioxin-6-yl)ethyl]phthalimide

In a stirred autoclave, 40 g of the product obtained according to Example 27 were initially charged dissolved in 100 ml of tetrahydrofuran, 2 g of palladium on carbon (10% by weight) were added and the mixture was hydrogenated at 50° C. and a hydrogen pressure of 10 bar until the reaction had gone to completion (about 22 hours). The catalyst was then filtered off and the solvent was removed. This gave 38.7 g of product. According to GC, stated in area per cent, the product was 57% pure. The yield was 55% of theory.

Example 29

2-(2,2,3 ,3-Tetrafluorobenzene[1,4]dioxin-6-yl)ethylamine 35 g of the product obtained according to Example 28 were initially charged in 80 ml of toluene and the mixture was heated to 75° C. 12.2 g of hydrazine monohydrate were then added dropwise. The mixture was stirred at 75° C. for 3 hours. 29.1 g of 25% by weight strength aqueous potassium hydroxide solution were then added dropwise and stirring was continued for a further 30 min. After cooling, the aqueous (heaviest) phase and an organic oily (middle) phase were separated off. The toluene, being the lightest organic phase, was slowly distilled off. The residue was suspended in 50 ml of n-hexane and filtered. The filtrate was subsequently concentrated. This gave 8.7 g of product. According to GC, stated in area per cent, the product was 90% pure. This corresponds to a yield of 60% of theory.

Example 30

N-[2-(4-trifluorometh[]oxyphenyl)ethenyl]succinimide 55 ml of dry dimethylformamide were flushed with nitrogen for 30 minutes. 18.6 g of 1-bromo-4-(trifluoromethoxy)

benzene, 9.7 g of N-vinylsuccinimide, 19.3 mg of palladium (II) acetate, 24 mg of tri(o-tolyl)phosphine and 13 g of sodium acetate were added successively and the mixture was stirred at 130° C. for 20 hours. After cooling, the mixture was filtered, the filtrate was concentrated and the residue was suspended in 300 ml of water and filtered. The filtration residue was washed with 300 ml of n-hexane and dried. This gave 15.7 g of product of melting point 141–143° C. According to GC, stated in area per cent, the product was 94.6% pure. This corresponds to a yield of 67% of theory.

Example 31

N-[2-(4-Trifluoromethoxyphenyl)ethyl]succinimide

In a stirred autoclave, 21.4 g of the product obtained according to Example 30 were initially charged dissolved in. 100 ml of tetrahydrofuran, 0.5 g of palladium on carbon 5 (10% by weight) were added and the mixture was hydrogenated at 50° C. and a hydrogen pressure of from 5 to 10 bar until the reaction had gone to completion (about 4 hours). The catalyst was then filtered off and the solvent was removed. This gave 16.7 g of product of melting point 91–93° C. According to GC, stated in area per cent, the product was 95.9% pure. The yield was 78% of theory.

Example 32

2-(4-Trifluoromethoxyphenyl)ethylamine 15.4 g of the product obtained according to Example 31 were initially charged in 40 ml of toluene and the mixture was heated to 75° C. 7.2 g of hydrazine monohydrate were then added dropwise. The mixture was stirred at 75° C. for 8 hours. 17.3 g of 25% by weight strength aqueous potassium hydroxide solution were then added dropwise and stirring was continued for a further 60 min. After cooling, the aqueous (heaviest) phase and an organic oily (middle) phase were separated off. The toluene, being the lightest organic phase, was slowly distilled off and the residue was distilled under reduced pressure using a short Vigreux column. This gave 6.4 g of product which distilled over at from 82 to 84° C./12 mbar. According to GC, stated in area per cent, the product was 99.1% pure. This corresponds to a yield of 61% of theory.

What is claimed is:

1. A process for preparing fluorine-containing phenethylamines of the formula

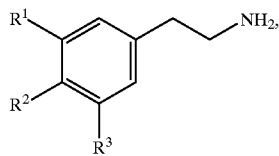

(I)

in which one of the radicals
$R^1$ and $R^2$ represents fluorine, trifluoromethyl, trifluoromethoxy, tetrafluoroethoxy or pentafluoroethoxy and the other represents hydrogen, $C_1$–$C_6$-alkyl, $C_1$–$C_6$-alkoxy, fluorine, trifluoromethyl, trifluoromethoxy, tetrafluoroethoxy or pentafluoroethoxy or
$R^1$ and $R^2$ together represent —O—$CF_2$—O—, —O—$CF_2$—$CF_2$— or —O—$CF_2$—$CF_2$—O— and
$R^3$ represents hydrogen, $C_1$–$C_6$-alkyl or $C_1$–$C_6$-alkoxy, in which in a first step a substituted bromobenzene of the formula

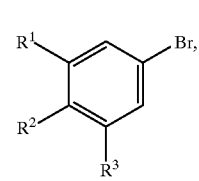

(IV)

in which
$R^1$, $R^2$ and $R^3$ are each as defined under formula (I) is reacted with an N-vinylimide of the formula

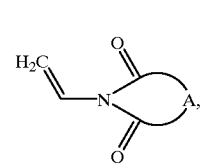

(V)

in which
A represents —$CH_2$—$CH_2$—, —$CH_2$—$CH_2$—$CH_2$—, —$CH_2$—$C(CH_3)_2$—$CH_2$—, —$CH_2$—O—$CH_2$—, —CH=CH— or o-phenylene,
in the presence of a palladium catalyst, to produce β-iminovinylbenzene of the formula

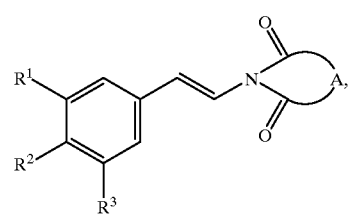

(III)

in which
the radicals $R^1$, $R^2$ and $R^3$ are each as defined under formula (I) and the radical A is as defined under formula (V)
is, in a second step, hydrogenated with catalyst and, in a third step, the substituted β-iminoethylbenzene of the formula

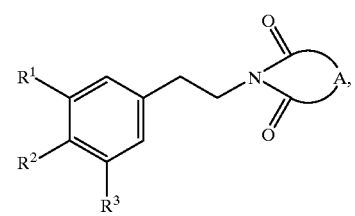

(II)

in which
$R^1$, $R^2$ and $R^3$ are each as defined under formula (I) and A is as defined under formula (V),
the imide moiety, is cleaved.

2. The process of claim 1, in which in the formulae (I), (II), (III) and (IV) one of the radicals $R^1$ and $R^2$ represents a radical from the group consisting of fluorine, trifluoromethyl, trifluoromethoxy, tetrafluorethoxy or pentafluoro-ethoxy and the other radical represents hydrogen or R¹ and R² together represent —O—CF$_2$—O—, —O—CF$_2$—CF$_2$— or —O—CF$_2$—CF$_2$—O—, R³ represents hydrogen and A in the formulae (II), (III) and (V) represents —CH$_2$—CH$_2$—or o-phenylene.

3. The process of claim 1, in which the palladium catalyst used in the first step is a palladium complex having aryl- or alkylphosphine ligands, the diluent used is a dipolar solvent and the reaction auxiliary is a weak inorganic or organic base and the reaction is carried out at temperatures between 50 and 180° C.

4. The process of claim 1, in which the second step is carried out using hydrogen in the presence of a diluent and in the presence of supported noble metals as catalyst.

5. The process of claim 1, in which the second reaction step is carried out in the presence of water or organic solvents as diluent, that 0.01 to 0.5 mol of catalyst (calculated as metal) is used per mole of β-iminovinylbenzene of the formula (III) and the reaction temperature is between 0 and 100° C.

6. The process according to claim 1, in which the third step is carried out in aqueous bases at temperatures of from 50 to 100° C.

7. The process of claim 1, in which in the third step between 1.2 and 5 equivalents of hydrazine hydrate is used per mole of imide of formula (II).

8. The process of claim 7, in which in the third step additionally between 1 and 30 mol of aqueous alkali metal hydroxide are employed per mole of imide of the formula (II).

* * * * *